United States Patent [19]
Liang

[11] Patent Number: 5,474,761
[45] Date of Patent: *Dec. 12, 1995

[54] ORAL COMPOSITIONS FOR TREATING PLAQUE AND GINGIVITIS

[75] Inventor: Nong Liang, West Chester, Ohio

[73] Assignee: The Procter & Gamble Company, Cincinnati, Ohio

[ * ] Notice: The term of this patent shall not extend beyond the expiration date of Pat. No. 5,290,542.

[21] Appl. No.: 201,599

[22] Filed: Feb. 25, 1994

Related U.S. Application Data

[63] Continuation-in-part of Ser. No. 153,238, Nov. 15, 1993, abandoned, which is a continuation of Ser. No. 45,743, Apr. 8, 1993, Pat. No. 5,290,542.

[51] Int. Cl.$^6$ .............................. A61K 7/16; A61K 7/18
[52] U.S. Cl. ............................................ 424/52; 424/49
[58] Field of Search .......................................... 424/49–52

[56] References Cited

U.S. PATENT DOCUMENTS

| | | | |
|---|---|---|---|
| 4,022,880 | 5/1977 | Vinson et al. | 424/49 |
| 4,293,544 | 10/1981 | Elmi | 424/60 |
| 4,512,987 | 4/1985 | Schindlery | 514/171 |
| 4,568,480 | 2/1986 | Thir et al. | 252/312 |
| 4,656,031 | 4/1987 | Lane et al. | 424/49 |
| 4,767,751 | 8/1988 | Davis | 514/179 |
| 4,835,002 | 5/1989 | Wolf et al. | 426/590 |
| 4,842,766 | 6/1989 | Blehm et al. | 252/309 |
| 4,894,220 | 1/1990 | Nabi et al. | 424/52 |
| 4,940,701 | 7/1990 | Davis | 514/179 |
| 4,971,788 | 11/1990 | Tabibi et al. | 424/49 |
| 4,980,153 | 12/1990 | Jackson et al. | 424/52 |
| 4,992,259 | 2/1991 | Schiraldi et al. | 424/49 |
| 5,032,385 | 7/1991 | Reed et al. | 424/49 |
| 5,032,386 | 7/1991 | Gaffar et al. | 424/49 |
| 5,037,635 | 8/1991 | Nabi et al. | 424/52 |
| 5,045,337 | 9/1991 | El-Nokaly et al. | 426/602 |
| 5,130,122 | 7/1992 | Tabibi et al. | 424/49 |
| 5,145,667 | 9/1992 | Ibrahim et al. | 424/52 |
| 5,156,835 | 10/1992 | Nabi et al. | 424/52 |
| 5,160,669 | 11/1992 | Wallach et al. | 264/4.3 |
| 5,162,378 | 11/1992 | Guthauser | 514/785 |
| 5,167,951 | 12/1992 | Gaffar et al. | 424/49 |
| 5,178,851 | 1/1993 | Gaffar et al. | 424/52 |
| 5,180,577 | 1/1993 | Polefka et al. | 424/52 |
| 5,180,578 | 1/1993 | Gaffar et al. | 424/52 |
| 5,188,822 | 2/1993 | Viccard et al. | 424/52 |
| 5,190,915 | 3/1993 | Behan et al. | 512/2 |
| 5,234,495 | 8/1993 | Breneman et al. | 106/287.1 |
| 5,236,699 | 8/1993 | Libin | 424/54 |
| 5,283,056 | 2/1994 | Chung et al. | 424/49 |
| 5,284,648 | 2/1994 | White et al. | 424/59 |
| 5,290,541 | 3/1994 | Liang | 424/49 |
| 5,290,542 | 3/1994 | Liang | 424/52 |

FOREIGN PATENT DOCUMENTS

| 1177756 | 11/1984 | Canada . |
| 161899 | 9/1984 | European Pat. Off. . |
| 161898 | 9/1984 | European Pat. Off. . |
| 0278660 | 8/1988 | European Pat. Off. . |
| 2200551 | 8/1988 | United Kingdom . |

Primary Examiner—Shep K. Rose
Attorney, Agent, or Firm—Douglas C. Mohl; David K. Dabbiere; Jacobus C. Rasser

[57] ABSTRACT

Disclosed are oral compositions which are effective against plaque and gingivitis and contain a noncationic water insoluble antibacterial agent.

12 Claims, No Drawings

ORAL COMPOSITIONS FOR TREATING PLAQUE AND GINGIVITIS

CROSS REFERENCE TO RELATED APPLICATION

This is a continuation-in-part of application Ser. No. 153,238 filed Nov. 15, 1993 now abandoned which is a continuation of application Ser. No. 045,743, filed Apr. 8, 1993 now U.S. Pat. No. 5,290,542.

TECHNICAL FIELD

The present invention relates to oral compositions which provide antiplaque and antigingivitis benefits as well as being effective against other anaerobic infections of the mouth.

Plaque induced diseases, including periodontitis and gingivitis, are believed to involve anaerobic bacterial infections. Periodontal disease affects the periodontium, which is the investing and supporting tissue surrounding a tooth (i.e., the periodontal ligament, the gingiva, and the alveolar bone). Gingivitis and periodontitis are inflammatory disorders of the gingiva and the periodontal ligament, respectively. Gingivosis and periodontosis are more severe conditions involving degenerative disorders of the tissue. Combinations of inflammatory and degenerative conditions are termed periodontitis complex.

Periodontal disease is a major cause of tooth loss in adults. Tooth loss from periodontal disease is a significant problem beginning at age 35, but even by age 15 it is estimated that about 4 out of 5 persons already have gingivitis and 4 out of 10 have periodontitis.

While good oral hygiene, as achieved by brushing the teeth with a cleansing dentifrice, may help reduce the incidence of periodontal disease, it does not necessarily prevent or eliminate its occurrence. This is because microorganisms contribute to both the initiation and progress of periodontal disease. Thus, in order to prevent or treat periodontal disease, these microorganisms must be suppressed by some means other than simple mechanical scrubbing. Towards this end, there has been a great deal of research aimed at developing therapeutic dentifrices, mouthwashes, and methods of treating periodontal disease which are effective in suppressing these microorganisms.

The use of noncationic, water-insoluble antibacterial agents in oral products is disclosed in a number of references. One such reference is U.S. Pat. No. 4,022,889 to Vinson et al. Vinson describes compositions containing zinc salts and antibacterial agents such as halogenated salicylanilides and halogenated hydroxydiphenyl ethers.

Another reference disclosing noncationic water-insoluble antibacterial agents is U.K. Patent Application GB 2,200,551, published Aug. 10, 1988. In addition to the antibacterial, the compositions contain a molecularly dehydrated polyphosphate salt. The salt is stated to improve the effectiveness of the antibacterial. All prior art references are included herein in total by reference.

It has now been found that the bioavailability and effectiveness of the antibacterial can be improved significantly by combining the antibacterial with a bicarbonate salt, preferably sodium bicarbonate. This allows for the antibacterial to be more effectively deposited on the surfaces of the mouth and better mouth feel to be obtained.

It is therefore an object of the present invention to provide improved products containing antibacterial agents.

It is a further object of the present invention to provide more effective products for treating diseases of the oral cavity.

It is still a further object to provide methods for treating diseases of the oral cavity.

These and other objects will become readily apparent from the disclosure which follows.

All percentages and ratios used herein are by weight of the total composition unless otherwise specified. Also, all measurements referred to herein are made at 25° C. in the composition unless otherwise specified.

SUMMARY OF THE INVENTION

The present invention, in certain aspects, embraces compositions containing a water-insoluble noncationic antibacterial agent and a bicarbonate salt.

The present invention also encompasses a method for treating diseases of the oral cavity using the specified compositions.

By "oral compositions" as used herein means a product which in the ordinary course of usage is not intentionally swallowed for purposes of systemic administration of particular therapeutic agents, but is rather retained in the oral cavity for a time sufficient to contact substantially all of the dental surfaces and/or oral tissues for purposes of oral activity.

By "safe and effective amount" as used herein means sufficient mount of material to provide the desired benefit while being safe to the hard and soft tissues of the oral cavity.

By the term "comprising", as used herein, is meant that various additional components can be conjointly employed in the compositions of this invention as long as the listed materials perform their intended functions.

By the term "carder", as used herein, is meant a suitable vehicle which is pharmaceutically acceptable and can be used to apply the present compositions in the oral cavity.

DETAILED DESCRIPTION OF THE INVENTION

The present invention in a certain aspect involves forming a composition containing a bicarbonate salt and a water-insoluble, noncationic antibacterial. The essential and optional components of the compositions are set forth in detail below. The compositions of this invention are preferably substantially free of potassium ions (e.g. less than about 0.001% potassium ions).

ESSENTIAL COMPONENTS

Antibacterial Agents

Given below are examples of antibacterial agents useful in the compositions of the present invention which are water insoluble and noncationic.

Halogenated Diphenyl Ethers

2',4,4'-trichloro-2-hydroxy-diphenyl ether (Triclosan)
2,2'-dihydroxy-5,5'-dibromo-diphenyl ether.

Phenolic Compounds (including phenol and its homologs, mono- and polyalkyl and aromatic halophenols, resorcinol and its derivatives, bisphenolic compounds and halogenated salicylanilides).

Phenol and its Homologs

Phenol

| | |
|---|---|
| 2 Methyl | Phenol |
| 3 Methyl | Phenol |
| 4 Methyl | Phenol |
| 4 Ethyl | Phenol |
| 2,4-Dimethyl | Phenol |
| 2,5-Dimethyl | Phenol |
| 3,4-Dimethyl | Phenol |
| 2,6-Dimethyl | Phenol |
| 4-n-Propyl | Phenol |
| 4-n-Butyl | Phenol |
| 4-n-Amyl | Phenol |
| 4-tert-Amyl | Phenol |
| 4-n-Hexyl | Phenol |
| 4-n-Heptyl | Phenol |

Mono- and Poly-Alkyl and Aromatic Halophenols p-Chlorophenol

| | |
|---|---|
| Methyl | p-Chlorophenol |
| Ethyl - p-Chlorophenol | |
| n-Propyl | p-Chlorophenol |
| n-Butyl | p-Chlorophenol |
| n-Amyl | p-Chlorophenol |
| sec-Amyl | p-Chlorophenol |
| n-Hexyl | p-Chlorophenol |
| Cyclohexyl | p-Chlorophenol |
| n-Heptyl | p-Chlorophenol |
| n-Octyl | p-Chlorophenol | o-Chlorophenol

| | |
|---|---|
| Methyl | o-Chlorophenol |
| Ethyl - o-Chlorophenol | |
| n-Propyl | o-Chlorophenol |
| n-Butyl | o-Chlorophenol |
| n-Amyl | o-Chlorophenol |
| tert-Amyl | o-Chlorophenol |
| n-Hexyl | o-Chlorophenol |
| n-Heptyl | o-Chlorophenol |
| o-Benzyl | p-Chlorophenol |
| o-Benxyl-m-methyl | p-Chlorophenol |
| o-Benzyl-m, m-dimethyl | p-Chlorophenol |
| o-Phenylethyl | p-Chlorophenol |
| o-Phenylethyl-m-methyl | p-Chlorophenol |
| 3-Methyl | p-Chlorophenol |
| 3,5-Dimethyl | p-Chlorophenol |
| 6-Ethyl-3-methyl | p-Chlorophenol |
| 6-n-Propyl-3-methyl | p-Chlorophenol |
| 6-iso-Propyl-3-methyl | p-Chlorophenol |
| 2-Ethyl-3,5-dimethyl | p-Chlorophenol |
| 6-sec-Butyl-3-methyl | p-Chlorophenol |
| 2-iso-Propyl-3,5-dimethyl | p-Chlorophenol |
| 6-Diethylmethyl-3-methyl | p-Chlorophenol |
| 6-iso-Propyl-2-ethyl-3-methyl | p-Chlorophenol |
| 2-sec-Amyl-3,5-dimethyl | p-Chlorophenol |
| 2-Diethylmethyl-3,5-dimethyl | p-Chlorophenol |
| 6-sec-Octyl-3-methyl | p-Chlorophenol | p-Bromophenol

| | |
|---|---|
| Methyl | p-Bromophenol |
| Ethyl | p-Bromophenol |
| n-Propyl | p-Bromophenol |
| n-Butyl | p-Bromophenol |
| n-Amyl | p-Bromophenol |
| sec-Amyl | p-Bromophenol |
| n-Hexyl | p-Bromophenol |
| cyclohexyl | p-Bromophenol | o-Bromophenol

| | |
|---|---|
| tert-Amyl | o-Bromophenol |
| n-Hexyl | o-Bromophenol |
| n-Propyl-m,mDimethyl | o-Bromophenol |

2-Phenyl Phenol
4-Chloro-2-methyl phenol
4-Chloro-3-methyl phenol
4-Chloro-3,5-dimethyl phenol
2,4-dichloro-3,5-dimethylphenol
3,4,5,6-terabromo-2-methylphenol
5-methyl-2-pentylphenol
4-isopropyl-3-methylphenol
5-Chloro-2-hydroxydiphenyl-methane

Resorcinol and its Derivatives

Resorcinol

| | |
|---|---|
| Methyl | Resorcinol |
| Ethyl | Resorcinol |
| n-Propyl | Resorcinol |
| n-Butyl | Resorcinol |
| n-Amyl | Resorcinol |
| n-Hexyl | Resorcinol |
| n-Heptyl | Resorcinol |
| n-Octyl | Resorcinol |
| n-Nonyl | Resorcinol |
| Phenyl | Resorcinol |
| Benzyl | Resorcinol |
| Phenylethyl | Resorcinol |
| Phenylpropyl | Resorcinol |
| p-Chlorobenzyl | Resorcinol |
| 5-Chloro | 2,4-Dihydroxydiphenyl Methane |
| 4'-Chloro | 2,4-Dihydroxydiphenyl Methane |
| 5-Bromo | 2,4-Dihydroxydiphenyl Methane |
| 4'-Bromo | 2,4-Dihydroxydiphenyl Methane |

Bisphenolic Compounds 2,2'-methylene bis (4-chlorophenol)
2,2'-methylene bis (3,4,6-trichlorophenol)
2,2'-methylene bis (4-chloro-6-bromophenol)
bis (2-hydroxy-3,5-dichlorophenyl) sulphide
bis (2-hydroxy-5-chlorobenzyl) sulphide

Halogenated Salicylanilides

4',5-dibromosalicylanilide
3,4',5-trichlorosalcylanilide
3,4',5-tribromosalicylanilide
2,3,3',5-tetrachlorosalicylanilide
3,3',5-trichlorosalicylanilide
3,5-dibromo-3'-trifluoromethyl salicylanilide
5-n-octanoyl-3'-trifluoromethyl salicylanilide
3,5-dibromo-4'-trifluoromethyl salicylanilide
3,5-dibromo-3'-trifluoromethyl salicylanilide
(Fluorophene)

Benzoic Esters p-Hydroxybenzoic Acid

| | |
|---|---|
| Methyl | p-Hydroxybenzoic Acid |
| Ethyl | p-Hydroxybenzoic Acid |
| Propyl | p-Hydroxybenzoic Acid |
| Butyl | p-Hydroxybenzoic Acid |

Halogenated Carbanilides 3,4,4'-trichlorocarbanilide
3-trifluoromethyl-4,4'-dichlorocarbanilide
3,3',4-trichlorocarbanilide The antibacterial agent is present in the oral composition prepared in an effective antiplaque amount, typically about 0.01–5% by weight, preferably about 0.03–1%. The antibacterial agent is substantially water-insoluble, meaning that its solubility is less than about 1% by weight in water at 25° C. and may be even less than about 0.1%. If an ionizable group is present solubility is determined at a pH at which ionization does not occur.

Surfactants

The surfactants useful in the compositions of this invention include many different surfactants. Suitable surfactants include any which are reasonably stable and function over a wide pH range. Included are non-soap anionic, nonionic, cationic, zwitterionic and amphoteric organic synthetic surfactants. Many of these are disclosed by Gieseke et al. in U.S. Pat. No. 4,051,234, Sep. 27, 1988 incorporated herein in total by reference.

Preferred surfactants include alkyl sulfates. The surfactant is generally present at a level of from about 0.2% to about 7% preferably from about 0.6% to about 4.0%.

Water

Water is also present in the preferred compositions of this invention. Water employed in the preparation of commercially suitable compositions should preferably be deionized and free of organic impurities. Water generally comprises from about 10% to 50%, preferably from about 20% to 40%, by weight of the toothpaste compositions herein while mouthwashes contain from about 40% to about 95%, preferably 50–80%. These amounts of water include the free water which is added plus that which is introduced with other materials as with sorbitol.

Solvent

A solvent is present in the compositions of the present invention. The solvent is used to solubilize the antibacterial and can be any number of agents.

Preferred agents include flavor oils such as those mentioned subsequently or agents such as polyethylene glycols, preferably those having molecular weights of from about 200 to about 600, propylene glycol, dipropylene glycol, methyl cellosolve, ethyl cellosolve, olive oil, castor oil, amylacetate, ethyl acetate, glyceryl tristearate, benzyl benzoate and mixtures thereof. The solvent is used generally in an amount of from about 1 to about 10% preferably from about 2 to about 6%.

Bicarbonate Salt

Another essential component of the present compositions is a bicarbonate salt preferably an alkali metal salt. The preferred bicarbonate salt is sodium bicarbonate which is a staple item of commerce. The bicarbonate is usually used at a level of from about 1 to about 50, preferably from about 1.5 to about 25, most preferably about 5 to about 25 percent.

Optional Components

The compositions of the present invention may contain in addition to the above-listed components many others which will be somewhat dependent on the type of composition (mouthwashes, toothpastes, topical gels, prophylaxis pastes and the like). Toothpastes and mouthwashes are the preferred systems with toothpastes being the most preferred.

Toothpastes contain as a major component an abrasive. The abrasive polishing material contemplated for use in the present invention can be any material which does not excessively abrade dentin. These include, for example, silicas including gels and precipitates, calcium carbonate, dicalcium orthophosphate dihydrate, calcium pyrophosphate, tricalcium phosphate, calcium polymetaphosphate, insoluble sodium polymetaphosphate, hydrated alumina, and resinous abrasive materials such as particulate condensation products of urea and formaldehyde, and others such as disclosed by Cooley et al. in U.S. Pat. No. 3,070,510, Dec. 25, 1962, incorporated herein by reference. Mixtures of abrasives may also be used.

Silica dental abrasives, of various types, can provide the unique benefits of exceptional dental cleaning and polishing performance without unduly abrading tooth enamel or dentin. Silica abrasive materials are also exceptionally compatible with sources of soluble fluoride and other ion sources. For these reasons they are preferred for use herein.

The silica abrasive polishing materials useful herein, as well as the other abrasives, generally have an average particle size ranging between about 0.1 and 30 microns, preferably 5 and 15 microns. The silica abrasive can be precipitated silica or silica gels such as the silica xerogels described in Pader et al., U.S. Pat. No. 3,538,230, issued Mar. 2, 1970 and DiGiulio, U.S. Pat. No. 3,862,307, Jun. 21, 1975, both incorporated herein by reference. Preferred are the silica xerogels marketed under the tradename "Syloid" by the W.R. Grace & Company, Davison Chemical Division. Preferred precipitated silica materials include those marketed by the J.M. Huber Corporation under the tradename, "Zeodent", particularly the silica carrying the designation "Zeodent 119". These silica abrasives are described in U.S. Pat. No. 4,340,583, Jul. 29, 1982, incorporated herein by reference.

The abrasive in the dentifrice compositions described herein is present at a level of from about 6% to about 70%, preferably from about 15% to about 30% when the dentifrice is a toothpaste.

Flavoring agents, as was noted earlier, can also be added to the dentifrice and other compositions of the present invention. Suitable flavoring agents include oil of wintergreen, oil of peppermint, oil of spearmint, oil of sassafras, and oil of clove. Sweetening agents are also useful and include aspartame, acesulfame, saccharin, dextrose, levulose and sodium cyclamate. Flavoring and sweetening agents are generally used in the compositions herein at levels of from about 0.005% to about 2% by weight and may be used as a solvent for the antibacterials hereinbefore indicated.

In preparing toothpastes, it is necessary to add some thickening material to provide a desirable consistency. Preferred thickening agents are carboxyvinyl polymers, carrageenan, hydroxyethyl cellulose and water soluble salts of cellulose ethers such as sodium carboxymethyl cellulose and sodium carboxymethyl hydroxyethyl cellulose. Natural gums such as gum karaya, gum arabic, and gum tragacanth and polysaccharide gums such as xanthan gum can also be used. Colloidal magnesium aluminum silicate or finely divided silica can be used as part of the thickening agent to further improve texture. Thickening agents in a combined amount from 0.5% to 5.0% by weight of the total composition may be used.

It is also desirable to include a humectant in a toothpaste to keep it from hardening. Suitable humectants include glycerin, sorbitol, and other edible polyhydric alcohols at a level of from about 10% to about 70%.

Another preferred embodiment of the present invention is a mouthwash composition. Mouthwashes generally comprise from about 20:1 to about 2:1 of a water/ethyl alcohol solution and preferably other ingredients such as flavor, sweeteners, humectants and sudsing agents such as those described above. The humectants, such as glycerin and sorbitol give a moist feel to the mouth. Generally, on a weight basis the mouthwashes of the invention comprise 5% to 60% (preferably 10% to 25%) ethyl alcohol, 0% to 20% (preferably 5% to 20%) of a humectant, 0% to 2% (preferably 0.01% to 0.15%) emulsifying agent, 0% to 0.5% (preferably 0.005% to 0.06%) sweetening agent such as saccharin, 0% to 0.3% (preferably from 0.03% to 0.3%) flavoring agent, and the balance water.

The pH of the present compositions and/or its pH in the mouth can be any pH which is safe for the mouth's hard and soft tissues. Such pH's are generally from about 5 to about 10, preferably from about 8.5 to about 9.5.

Another optional component of the compositions of this invention is an anionic polycarboxylate. The anionic polymeric polycarboxylates optionally but preferably employed herein are well known, being employed in the form of their free acids or partially or preferably fully neutralized water soluble alkali metal (e.g. preferably sodium) or ammonium salts. Preferred are 1:4 to 4:1 copolymers of maleic anhydride or acid with another polymerizable ethylenically unsaturated monomer, preferably methyl vinyl ether (methoxyethylene) having a molecular weight (M.W.) of about 30,000 to about 1,000,000. These copolymers are available for example as Gantrez (AN 139(M.W. 500,000), A.N. 119 (M.W. 250,000) and preferably S-97 Pharmaceutical Grade (M.W. 70,000), of GAF Corporation.

Other operative polymeric polycarboxylates include those such as the 1: 1 copolymers of maleic anhydride with ethyl acrylate, hydroxyethyl methacrylate, N-vinyl- 2-pyrollidone, or ethylene, the latter being available for example as Monsanto EMA No. 1103, M.W. 10,000 and EMA Grade 61, and 1:1 copolymers of acrylic acid with methyl or hydroxyethyl methacrylate, methyl or ethyl acrylate, isobutyl vinyl ether or N-vinyl-2-pyrrolidone.

Additional operative polymeric polycarboxylates disclosed in above referred to U.S. Pat. Nos. 4,138,477 and 4,183,914, incorporated herein by reference, include copolymers of maleic anhydride with styrene, isobutylene or ethyl vinyl ether, polyacrylic, polyitaconic and polymaleic acids, and sulfoacrylic oligomers of M.W. as low as 1,000 available as Uniroyal ND-2.

Suitable generally are polymerized olefinically or ethylenically unsaturated carboxylic acids containing an activated carbon-to-carbon olefinic double bond and at least one carboxyl group, that is, an acid containing an olefinic double bond which readily functions in polymerization because of its presence in the monomer molecule either in the alpha-beta position with respect to a carboxyl group or as part of a terminal methylene grouping. Illustrative of such acids are acrylic, methacrylic, ethacrylic, alpha-chloroacrylic, crotonic, beta-acyloxy propionic, sorbic, alpha-chlorsorbic, cinnamic, beta-styrylacrylic, muconic, itaconic, citraconic, mesaconic, glutaconic, aconitic, alpha-phenylacrylic, 2-benzyl acrylic, 2-cyclohexylacrylic, angelic, umbellic, fumaric, maleic acids and anhydrides. Other different olefinic monomers copolymerizable with such carboxylic monomers include vinylacetate, vinyl chloride, dimethyl maleate and the like. Copolymers contain sufficient carboxylic salt groups for water-solubility.

Also useful herein are carboxyvinyl polymers, referred to herein earlier as suitable binders, disclosed as toothpaste components in U.S. Pat. No. 3,980,767 issued Sep. 14, 1976 to Choun et al., U.S. Pat. No. 3,935,396 issued Jan. 27, 1976 to Roberts et al., U.S. Pat. No. 3,919,409 issued Nov. 11, 1975 to Peria et al., U.S. Pat. No. 3,911,904 issued Oct. 7, 1975 to Harrison, and U.S. Pat. No. 3,711,604 issued Jan. 16, 1973 to Colodney et al. They are commercially available for example under the trademarks Carbopol 934, 940, 941 and 956 of B. F. Goodrich, these products consisting essentially of a colloidally water-soluble polymer of polyacrylic acid crosslinked with from about 0.75% to about 2.0% of polyallyl sucrose or polyallyl pentaerythritol as crosslinking agent.

The synthetic anionic polymeric polycarboxylate component is mainly a hydrocarbon with optional halogen and O-containing substituents and linkages as present in for example ester, ether and OH groups, and when present is generally employed in the instant compositions in approximate weight amounts of 0.05 to 3%, preferably 0.05 to 2%, more preferably 0.1 to 2%.

Another optional component is a fluoride ion source. The sources of fluoride ions, or fluoride-providing compounds, useful according to this invention are well known in the art as anticaries agents and pyrophosphatase inhibitors and also act as such agents in the practice of this invention. These compounds may be slightly soluble in water or may be fully water-soluble. They are characterized by their ability to release fluoride ions in water and by freedom from undesired reaction with other compounds of the oral preparation. Among these materials are inorganic fluoride salts, such as soluble alkali metal, alkaline earth metal salts, for example, sodium fluoride, barium fluoride, sodium fluorsilicate, ammonium fluorosilicate, sodium fluorozirconate, sodium monofluorophosphate, aluminum mono- and di-fluorophosphate, and fluorinated sodium calcium pyrophosphate. Alkali metal and tin fluorides, such as sodium and stannous fluorides, sodium monofluorophosphate (MFP) and mixtures thereof, are preferred.

The amount of fluoride-providing compound is dependent to some extent upon the type of compound, its solubility, and the type of oral preparation, but it must be a nontoxic amount, generally about 0.005 to about 3.0% in the preparation. In a dentifrice preparation, e.g. dental gel, toothpaste (including cream), an amount of such compound which releases up to about 5,000 ppm of F ion by weight of the preparation is considered satisfactory. Any suitable minimum amount of such compound may be used, but it is preferable to employ sufficient compound to release about 300 to 2,000 ppm, more preferably about 800 to about 1,500 ppm of fluoride ion. Typically, in the cases of alkali metal fluorides and stannous fluoride, this component is present in an amount up to about 2% by weight, based on the weight of the preparation, and preferably in the range of about 0.05% to 1%. In the case of sodium monofluorophosphate, the compound may be present in an amount of about 0.1–3%, more typically about 0.76%.

Still another optional component for use in the compositions is a nonpolymeric anticalculus agent. These agents include any which are effective against calculus such as pyrophosphate salts as disclosed in U.S. Pat. No. 4,515,772, May 7, 1985 incorporated herein by reference. The preferred agents are mono, di, tri and tetra alkali metal and ammonium pyrophosphate. Such agents are used in amounts sufficient to reduce calculus. These amounts are preferably in an amount of at least about 1% $P_2O_7$, most preferably at least about 1.3%, most preferably at least about 1.5%.

Other anticalculus agents are metal ions such as zinc disclosed in U.S. Pat. No. 4,022,880, May 10, 1977 to Vinson incorporated herein by reference. Still others are polymers such as those described in U.S. Pat. No. 4,661,341, Apr. 28, 1987 to Benedict and U.S. Pat. No. 3,429,963, Feb. 25, 1969 to Shedlovsky, both of which are incorporated herein by reference. Such metals are used in an amount of from about 0.01% to about 5%, preferably about 0.1% to about 2%, while such polymers are used in amounts of from about 0.1% to about 10%, preferably from about 0.5% to about 5%.

Still other anticalculus agents are the diphosphonates such as those described in U.S. Pat. No. 3,988,443 and U.S. 3,488,419 incorporated herein by reference in their entirety.

Method of Manufacture

The compositions of the present invention can be prepared using the method described following the Examples.

Composition Use

The present invention in its method aspect involves applying to the oral cavity safe and effective amounts of the antimicrobial. Generally, amounts of at least about 0.001 g of the antimicrobial is effective.

Given below are two examples representative of the present invention. They describe and demonstrate preferred embodiments within the invention's scope.

The examples are given solely for the purpose of illustration and are not to be construed as limitations of this invention. Many variations thereof are possible without departing from the invention's spirit and scope.

EXAMPLE I

Given below is a tartar control version of the present invention.

| Component | Weight % |
| --- | --- |
| Triclosan | 0.450 |
| Sodium Fluoride (USP) | 0.243 |
| Tetrasodium Pyrophosphate, Anhydrous | 5.045 |
| Purified Water (USP) | 19.621 |
| Glycerin (USP) | 15.000 |
| Polyethylene Glycol 300 (NF) | 3.000 |
| Carboxymethyl Cellulose | 0.700 |
| Sodium Carbonate | 3.000 |
| Sodium Bicarbonate | 20.000 |
| Precipitated Silica | 18.000 |
| Titanium Dioxide (USP) | 0.350 |
| Sodium Alkyl Sulfate (28% Solution) | 4.000 |
| Saccharin, Sodium (USP) | 0.530 |
| Flavor | 1.000 |
| Sorbitol Solution (USP) | 9.061 |

The above composition is preferably prepared by making a series of premixes and combining them in a specified order.

1. Premix one consists of water, sorbitol, sodium fluoride, sodium saccharin, sodium carbonate, glycerin or other optional water soluble materials.
2. Premix two consists of the flavor, triclosan, polyethylene glycol and sodium alkly sulfate solution. p1 3. Premix three consists of sodium bicarbonate, titanium dioxide, silica and carboxymethyl cellulose.
4. Premix four consists of tetrasodium pyrophosphate and glycerin.

All premixes are thoroughly mixed and premix two is mixed for a time sufficient to fully solubilize the triclosan. The premixes are mixed together in the order given (i.e., premix two is mixed with premix one, then premix three is added to the mixture of one and two, etc.). When premix two is mixed with premix one, allow sufficient agitation and mixing time to ensure that the triclosan is solubilized in the water-soluble phenolate form, forming triclosan, flavor and surfactant microemulsion.

EXAMPLE II

Given below is another composition representative of the present invention.

| Component | Weight % |
| --- | --- |
| Triclosan | 0.450 |
| Sodium Fluoride (USP) | 0.243 |
| Purified Water (USP) | 24.666 |
| Glycerin (USP) | 15.000 |
| Polyethylene Glycol 300 (NF) | 3.000 |
| Carboxymethyl Cellulose | 0.700 |
| Sodium Carbonate | 3.000 |
| Sodium Bicarbonate | 20.000 |
| Precipitated Silica | 18.000 |
| Titanium Dioxide (USP) | 0.350 |
| Sodium Alkyl Sulfate (28% Solution) | 4.000 |
| Saccharin, Sodium (USP) | 0.530 |
| Flavor | 1.000 |
| Sorbitol Solution (USP) | 9.061 |

EXAMPLE III

Given below is another composition.

| Component | Weight % |
| --- | --- |
| Triclosan | 0.280 |
| Na Fluoride | 0.243 |
| Silica | 30.000 |
| RO Water | 23.954 |
| Glycerin | 13.000 |
| Sorbitol | 6.650 |
| SASS | 6.000 |
| TSPP | 5.045 |
| Na Bicarbonate | 5.000 |
| PEG 6 | 4.000 |
| Na Carbonate | 2.850 |
| Flavor BSTC | 1.100 |
| CMC 12M8P | 1.000 |
| Saccharin | 0.528 |
| TiO2 | 0.350 |
| pH | 9.0 |

What is claimed:

1. Aqueous oral compositions comprising a non-cationic, water-insoluble antibacterial agent, a solvent for said agent, a surfactant, from about 1.5% to about 50% a bicarbonate salt and water and wherein said composition has a neat pH of from about 8.5 to about 9.5 and said composition is substantially free of potassium ions.

2. A composition according to claim 1 wherein said solvent is a flavor oil and the bicarbonate salt is sodium bicarbonate.

3. A composition according to claim 1 wherein said solvent is a glycol.

4. A composition according to claim 1 wherein said solvent is a combination of flavoring oils and glycols.

5. A composition according to claim 2 wherein said composition is either a toothpaste or mouthwash.

6. A composition according to claim 5 wherein said toothpaste contains an abrasive.

7. A composition according to claim 6 wherein said toothpaste also contains triclosan as the antibacterial agent and the ratio of surfactant to antibacterial plus flavor is equal to or greater than the critical point where a microemulsion of the antibacterial will form.

8. A composition according to claim 7 wherein said toothpaste contains a soluble fluoride ion source.

9. A process for treating diseases of the oral cavity by applying to said cavity an effective mount of a composition according to claim 1.

10. A process for treating diseases of the oral cavity by applying to said cavity an effective amount of a composition according to claim 4.

11. A process for treating diseases of the oral cavity by applying to said cavity an effective amount of a composition according to claim 5.

12. A process for treating diseases of the oral cavity by applying to said cavity an effective amount of a composition according to claim 8.

* * * * *